United States Patent [19]

Task et al.

[11] Patent Number: 4,572,630
[45] Date of Patent: Feb. 25, 1986

[54] VARIABLE CONTRAST DIRECT READ-OUT VISION TESTER

[75] Inventors: Harry L. Task, Dayton, Ohio; Louis V. Genco, San Antonio, Tex.

[73] Assignee: The United States of America as represented by the Secretary of the Air Force, Washington, D.C.

[21] Appl. No.: 585,092

[22] Filed: Mar. 1, 1984

[51] Int. Cl.[4] ............................................. A61B 3/02
[52] U.S. Cl. ................................................. 351/243
[58] Field of Search ....................... 351/243, 244, 246

[56] References Cited

U.S. PATENT DOCUMENTS

| | | | |
|---|---|---|---|
| 1,981,587 | 11/1934 | Dorsey | 88/20 |
| 2,478,662 | 8/1949 | Long | 88/20 |
| 3,425,772 | 2/1969 | Minas | 351/246 |
| 3,469,904 | 9/1969 | Allen | 351/243 |
| 3,737,217 | 6/1973 | Haines et al. | 351/224 |
| 3,883,234 | 5/1975 | Lynn et al. | 351/224 |

Primary Examiner—Rodney B. Bovernick
Assistant Examiner—P. M. Dzierzynski
Attorney, Agent, or Firm—Donald J. Singer; Bobby D. Scearce

[57] ABSTRACT

A novel vision tester and vision testing method is described which comprises a pair of translucent displays, each transilluminated by electroluminescent lighting panels, the images of the two patterns being superimposed to provide a combined image characterized by a pattern of variable contrast. Light sensors near each light panel provide a measure of the relative intensities of the two images, which provides a measure of the contrast of each combined image. Contrast may be directly read out by processing the signals from the light sensors. The tester may be battery powered for portability.

15 Claims, 5 Drawing Figures

VARIABLE CONTRAST DIRECT READ-OUT VISION TESTER

RIGHTS OF THE GOVERNMENT

The invention described herein may be manufactured and used by or for the Government of the United States for all governmental purposes without the payment of any royalty.

BACKGROUND OF THE INVENTION

The present invention relates generally to vision testers and vision testing methods, and more particularly to a novel system and method for testing visual sensitivity of a subject to contrast.

The present invention provides a compact, portable, and battery operated system comprising electroluminescent lighting and light sensors used in conjunction with suitable control and microprocessor units to provide a vision test for sensitivity to contrast of various display configurations. A beam splitter superimposes the images of a test pattern and a neutral background density filter, each of which is transilluminated by an electroluminescent panel. The relative luminances of the two panels provide a measure of contrast. The microprocessor unit calculates the contrast based upon readings of light sensors disposed near each electroluminescent panel. The method incorporating the vision testing system of the invention combines variable contrast patterns, such as sine wave or square wave patterns of various frequencies, tri-bar patterns and spot patterns, and variable spatial frequency test patterns comprising resolution fans.

It is, therefore, a principal object of the present invention to provide an improved vision tester and method for testing visual sensitivity to contrast.

This and other objects of the present invention will become apparent as the detailed description of certain representative embodiments thereof proceeds.

SUMMARY OF THE INVENTION

In accordance with the foregoing principles and objects of the present invention, a novel vision tester and vision testing method is described which comprises a pair of translucent displays, each transilluminated by electroluminescent lighting panels, the images of the two patterns being superimposed to provide a combined image characterized by a pattern of variable contrast. Light sensors near each light panel provide a measure of the relative intensities of the two images, which provides a measure of the contrast of each combined image. Contrast may be directly read out by processing the signals from the light sensors. The tester may be battery powered for portability.

DESCRIPTION OF THE DRAWINGS

The present invention will be more clearly understood from the following detailed description of certain representative embodiments thereof read in conjunction with the accompanying drawings wherein.

DETAILED DESCRIPTION

Figure 1:
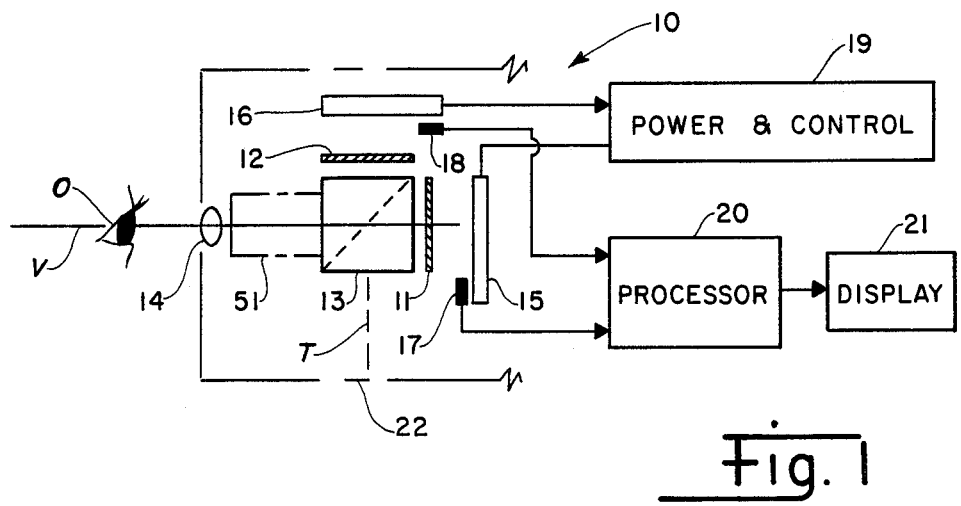
FIG. 1 is a schematic plan view of a representative optical system and related power, control, and information processing components comprising the present invention.

Referring now to the drawings, FIG. 1 presents a schematic plan view of a representative optical system and related electronic control, information processing and display components comprising the present invention. The testing system 10 of the invention comprises a translucent contrast display or test pattern 11 disposed for viewing by an observer/subject O along a first optical axis V. A translucent neutral density filter 12 is disposed for viewing along a second optical axis T perpendicular to and intersecting axis V. The representative patterns which may characterize test pattern 11 and neutral density filter 12, and the relationship between the patterns of each, are discussed below in relation to FIGS. 2, 3, and 4.

A beam splitter 13 is disposed at the intersection of axes V,T in order to reflect the image of neutral density filter 12 onto and along optical axis V and thereby to superimpose it onto the image of test pattern 11. An eyepiece lens 14 provides suitable collimation of the light comprising the superimposed images transmitted along viewing axis V for observation by subject O.

A first electroluminescent (EL) panel 15 is disposed along first optical (viewing) axis V near test pattern 11 for transilluminating pattern 11 for viewing by subject O. A substantially identical second electroluminescent panel 16 is disposed along axis T near neutral density filter 12 for transilluminating filter 12 to provide an image thereof for superimposition onto the image of pattern 11 at beam splitter 13. Other intensity controllable illuminating means may, within the scope of these teachings, be used to transilluminate test pattern 11 and filter 12. Light intensity measuring means in the form of first and second light sensors 17 and 18 are disposed, respectively, near panels 15,16 to measure the light level (luminance) of the two panels. Panels 15,16 may be provided with a suitable source of power and related control circuitry represented collectively in FIG. 1 by power and control electronics 19. Electronics 19 may include battery power in order to provide portability to system 10. The signals generated by the light sensors 17,18 may be received and processed by microcomputer processor electronics 20 for readout on display 21. The entire system 10 may be enclosed in a suitable housing 22 shown schematically in FIG. 1 by peripheral broken line.

Figure 2:
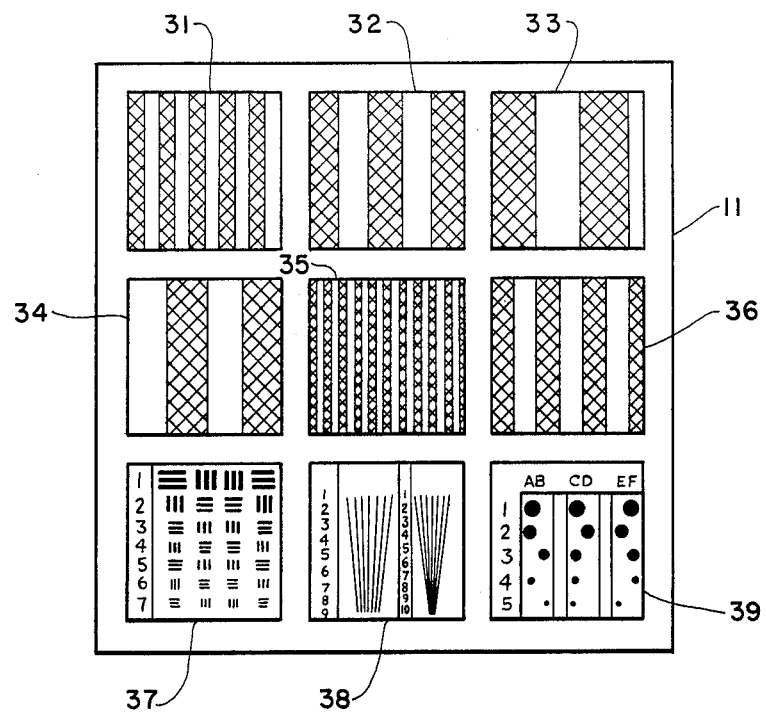
FIG. 2 is a representative visual test display pattern, on substantially enlarged scale, incorporating various contrast patterns for illumination and display for contrast sensitivity testing.

Referring now to FIG. 2, presented therein is a representative test pattern 11 comprising a photographic film or other transparency incorporating various contrast patterns for transillumination and display for contrast sensitivity testing. The representative test pattern 11 presented in FIG. 2 is shown on a substantially enlarged scale, as the pattern used in a representative system 10 built in demonstration of the invention herein comprised a film about 1.25 inches square, although it is understood that size is not limiting herein. Test pattern 11 may comprise any desirable variable density or spatial frequency configuration, such as shown in FIG. 2 as an array of a plurality of patterns including sine wave or square wave patterns 31–36 of various frequencies as illustrated, a tri-bar chart 37, one or more resolution fans 38, a dot pattern 39, or any desirable combination of such patterns which preferably are characterized by high inherent contrast. It is understood that any desirable selection of patterns may be used as would occur to one with skill in the field of this invention, those specifically mentioned herein being only representative of a multiplicity of such patterns which are suitable for use.

Figure 3:
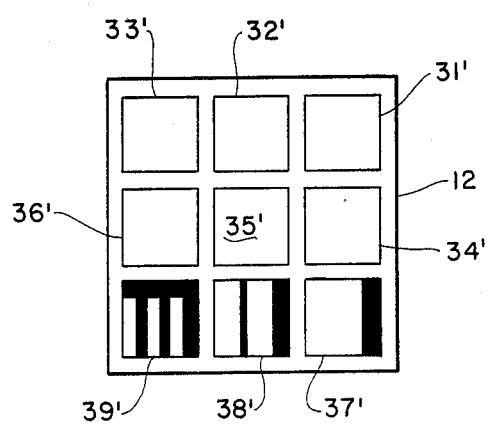
FIG. 3 is a schematic of the neutral density filter, on smaller scale than that of FIG. 2, and which is used in conjunction with the display of FIG. 2 for sensitivity testing.

Referring now to FIG. 3, presented therein is a schematic of a neutral density filter 12 for use as a reference with the test pattern 11 presented in FIG. 2. Filter 12 has the same physical size as test pattern 11, and the relative sizes illustrated in FIGS. 2 and 3 should therefore be ignored. Like test pattern 11, neutral density filter 12 comprises a photographic film or other transparancy having thereon an array of a plurality of patterns 31'–39'. Filter 12 is in function a neutral background density filter, but may preferably be configured in part as a mirror image of those areas of test pattern 11 that correspond to the identifying reference numerals and letters included on, for example, 37,38, 39 of test pattern 11 to facilitate subject identification of contrast patterns thereon. This arrangement allows the identifying numerals and letters to be easily visible at all times during a contrast sensitivity test.

For the purpose of discussion of the controlling principles of the present invention, the patterns 31–39 of test pattern 11 may be assumed to be characterized by a transmissivity $T_T$ on a background characterized by a different transmissivity $T_S$. The corresponding patterns 31'–39' of neutral density filter 12 may be characterized by a transmissivity $T_N$.

In the operation and use of the vision tester 10 of the present invention, subject O is positioned to observe the superimposed images of test pattern 11 and filter 12 as projected through beam splitter 13, as suggested in FIG. 1. By adjusting the relative luminances of the two electroluminescent panels 15, 16, the contrasts between the various patterns of test pattern 11 relative to the respective backgrounds can be varied.

The power and control circuit electronics 19 may provide single control change of contrast by increasing luminance of panel 15, while simultaneously decreasing the luminance of panel 16 (and vice versa). Light sensors 17,18 provide signals that are proportional, respectively, to the luminances of panels 15, 16. Processor electronics 20 then use these signals to determine the displayed contrast, which may be displayed on direct readout display 21.

Figure 4:
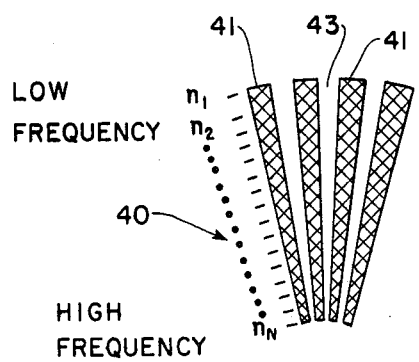
FIG. 4 is a schematic of a representative resolution fan useful as a spatial frequency pattern in determining contrast threshold according to the method of the present invention.

The processor calculates contrast C by the following equation:

$$C = \frac{T_B L_1 (T_T - T_S)}{L_1 T_B (T_T + T_S) + 2 R_B T_N L_2}$$

where:
C = Contrast;
$T_B$ = transmissivity of the beam splitter 13;
$R_B$ = reflectivity of the beam splitter 13;
$T_T$ = transmissivity of the patterns of the test pattern 11;
$T_S$ = transmissivity of the background of test pattern 11;
$T_N$ = transmissivity of the neutral density filter 12;
$L_1$ = luminance of EL panel 15 as measured by sensor 17;
$L_2$ = luminance of EL panel 16 as measured by sensor 18;

Referring now to FIG. 4, presented therein is a schematic of a representative resolution fan 40 which may be used with system 10 of the present invention to provide a novel method for testing contrast threshold. Such resolution fans may be that suggested in patterns 38 of test pattern 11 of FIG. 2. As shown in detail in FIG. 4, resolution fan 40 may comprise a pattern of radially extending areas 41 characterized by a first transmissivity (e.g., $T_T$ for the purposes of the above calculations), and separated by (background) areas 43 characterized by a different, second transmissivity (e.g., $T_S$). Resolution fan 40 may then be used with an appropriate neutral density filter within vision tester 10 as part of (or replacing) test pattern 11. The width and spacing of the areas comprising resolution fan 40 may be selected to provide a continuum of spatial frequencies $n_1$ to $n_N$ as suggested by the legend of FIG. 4. Using the continuum of spatial frequencies, the contrast may be set to a specific level and then the highest frequency resolvable taken as the dependent variable in the corresponding calculation of contrast using the above calculation. This allows contrast to be the independent variable in the calculations instead of the dependent variable as has characterized previously existing contrast measurement methods.

Figure 5:
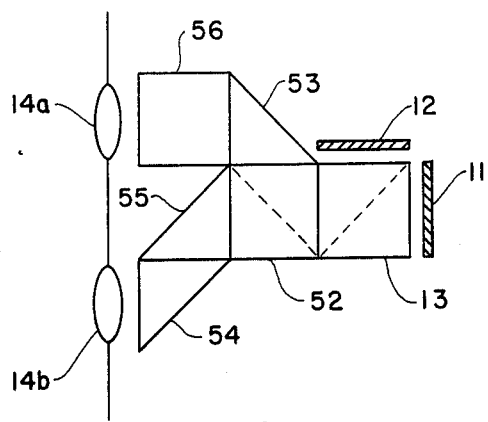
FIG. 5 is a schematic of a representative optical system useful to convert the optical system illustrated in FIG. 1 to a binocular display.

The vision testing system 10 as just described and depicted in FIG. 1 comprises a monocular system, although it is understood that the system could be configured as a binocular system by positioning two monocular systems 10 side by side for binocular viewing by subject O. Alternatively, as shown in FIG. 5, an optical system 51 comprising beam splitter 52, right-angle prisms 53, 54, 55 and an optical path length compensating cube 56 may be inserted into system 10 of FIG. 1 adjacent beam splitter 13 in order to divide the superimposed image for viewing through binocular eye-pieces 14a,14b.

The present invention, as hereinabove described, therefore provides a novel system and method for testing visual sensitivity to contrast. It is understood that certain modifications to the invention may be made, as might occur to one with skill in the field of this invention, within the scope of the appended claims. Therefore, all embodiments contemplated hereunder have not been shown in complete detail. Other embodiments may be developed without departing from the spirit of the invention or from the scope of the appended claims.

We claim:
1. A system for testing visual sensitivity of a subject to contrast, comprising:
 a. first and second translucent displays disposed for viewing along respective first and second optical axes, said displays having respective test and reference patterns thereon of first optical transmissivity on a background of second optical transmissivity;
 b. first and second light means disposed, respectively, near said first and second displays for transilluminating said displays;
 c. optical means for superimposing the images of said transilluminated displays for viewing by said subject along one of said axes;

d. means for controlling the respective light intensities of said first and second light means;
e. first and second light sensors disposed, respectively, near said first and second light means for measuring the light intensities of said light means and providing an output signal characteristic thereof; and
f. means for comparing the output signals of said light sensors to provide a measure of the relative contrasts of the transilluminated images of said first and second displays.

2. The system as recited in claim 1 wherein said first and second light means comprise a pair of electroluminescent panels.

3. The system as recited in claim 1 wherein said test pattern includes a resolution fan comprising a pattern of a plurality of radially extending alternate areas of first and second transmissivities.

4. The system as recited in claim 1 wherein said optical means for superimposing said first and second display images includes a beam splitter.

5. The system as recited in claim 1 wherein said test pattern includes a plurality of sine wave patterns of predetermined frequencies and characterized by predetermined varying degrees of transmissivity.

6. The system as recited in claim 5 wherein said reference display is uniformly transmissive with predetermined transmissivity.

7. The system as recited in claim 1 wherein said test pattern includes a plurality of square wave patterns of various frequencies characterized by alternate areas of predetermined high and low transmissivity values.

8. The system as recited in claim 1 wherein said test pattern includes a plurality of tri-bar patterns.

9. The system as recited in claim 1 further comprising binocular means, disposed adjacent said optical means, for providing binocular viewing of said images by said subject.

10. A method for testing visual sensitivity of a subject to contrast, comprising the steps of:
a. providing first and second translucent displays for viewing along respective first and second optical axes, said displays having respective test and reference patterns thereon of first optical transmissivity on a background of second optical transmissivity;
b. transilluminating said first and second displays to project the images thereof along the respective first and second axes;
c. optically imaging said second display image along said first axis and thereby superimposing said second display image onto said first display image along said first optical axis for viewing by said subject;
d. measuring the respective light intensities transilluminating said displays; and
e. comparing the respective intensities to provide a measure of the relative contrasts of the transilluminated images of said first and second displays.

11. The method as recited in claim 10 wherein said displays include a resolution fan comprising a pattern of a plurality of radially extending alternate areas of first and second transmissivities.

12. The method as recited in claim 10 wherein said first and second displays include a plurality of sine wave patterns of predetermined frequencies and characterized by predetermined varying degrees of transmissivity.

13. The method as recited in claim 12 wherein said reference display is uniformly transmissive with predetermined transmissivity.

14. The method as recited in claim 10 wherein said first and second displays include a plurality of square wave patterns of various frequencies characterized by alternate areas of predetermined high and low transmissivity values.

15. The method as recited in claim 10 wherein said first and second displays include a plurality of tri-bar patterns.

* * * * *